(12) United States Patent
Lieberman et al.

(10) Patent No.: US 7,260,283 B2
(45) Date of Patent: *Aug. 21, 2007

(54) DISTRIBUTED OPTICAL FIBER SENSOR WITH CONTROLLED RESPONSE

(75) Inventors: Robert A. Lieberman, Torrance, CA (US); Claudio O. Egalon, Redondo Beach, CA (US)

(73) Assignee: Optech Ventures, LLC, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/364,237

(22) Filed: Feb. 28, 2006

(65) Prior Publication Data

US 2006/0147149 A1  Jul. 6, 2006

Related U.S. Application Data

(60) Continuation of application No. 10/717,080, filed on Nov. 19, 2003, now Pat. No. 7,006,718, which is a continuation of application No. 09/730,158, filed on Dec. 5, 2000, now abandoned, which is a division of application No. 09/334,845, filed on Jun. 16, 1999, now Pat. No. 6,205,263.

(51) Int. Cl.
*G02B 6/00*  (2006.01)

(52) U.S. Cl. .................. 385/12; 385/122; 356/73.1
(58) Field of Classification Search ............... None
See application file for complete search history.

(56) References Cited

U.S. PATENT DOCUMENTS

| | | | | | |
|---|---|---|---|---|---|
| 4,560,248 | A | * | 12/1985 | Cramp et al. ................. | 385/12 |
| 4,881,793 | A | * | 11/1989 | Tarbox ....................... | 385/140 |
| 5,572,618 | A | * | 11/1996 | DiGiovanni et al. ........ | 385/140 |
| 5,930,435 | A | * | 7/1999 | Laming et al. ............. | 385/126 |
| 5,995,686 | A | * | 11/1999 | Hamburger et al. .......... | 385/12 |
| 6,097,874 | A | * | 8/2000 | Yunoki ....................... | 385/140 |
| 7,006,718 | B2 | * | 2/2006 | Lieberman et al. ........... | 385/12 |

* cited by examiner

*Primary Examiner*—Arnel Lavarias
(74) *Attorney, Agent, or Firm*—Lawrence S. Cohen

(57) ABSTRACT

Distributed fiber optic chemical and physical sensors provide a relatively highly uniform response over the length of the fiber by, for example, varying such properties as the core/cladding index of refraction ratio to compensate for the non-linearity in sensitivity due for example to the loss of higher order modes in multi-mode fibers. The variation of the ratio changes the absorption coefficient of the fiber and can be used to compensate for any non-linearity in response. Other techniques for compensation also are disclosed.

8 Claims, 3 Drawing Sheets

DISTRIBUTED OPTICAL FIBER SENSOR WITH CONTROLLED RESPONSE

This application is a continuation of application Ser. No. 10/717,080 filed on Nov. 19, 2003 U.S. Pat. No. 7,006,718 which is a continuation of application Ser. No. 09/730,158 filed on Dec. 5, 2000 abandoned which is a divisional of application Ser. No. 09/334,845 filed on Jun. 16$^{th}$, 1999 now U.S. Pat. No. 6,205,263. The entire content of each of the above referred application is incorporated herein by reference.

The invention was made which Government support under contract No NASA1-19895 and No NASA1-20206. The Government has certain rights in the invention.

FIELD OF INVENTION

This invention relates to optical fiber sensors and more particularly to such sensors which include materials in the coatings and/or claddings of optical fibers which produce changes in the characteristics of the light carried by the fiber responsive to the presence of a material or field to be detected.

BACKGROUND OF THE INVENTION

U.S. Pat. No. 4,834,496 issues May 30, 1989 discloses distributed fiber optic chemical sensors. Such a sensor comprises an optical fiber with a core and a cladding which is permeable. The cladding, or a coating on the cladding, includes a composition, the optical properties of which are altered in the presence of a material to be detected. The light (i.e. the wavelength of the intensity of the light) transmitted through the core of the fiber is a function of the change in optical properties caused by the interaction of the composition included in the permeable coating with the material to be detected. The change in optical properties may comprise (for example) a change in the index of refraction (or indices of refraction differential), or an increase or decrease in the optical absorbance of fluorescence of the composition.

The above-noted patent discloses materials, compositions, sensing parameters and examples of such sensors, all of which are useful in accordance with the principles of this invention. In addition, distributed fiber optic sensors for physical properties, such as temperature or pressure, can also be fabricated based on similar properties, e.g., temperature-induced or pressure-induced changes in the refractive index, optical absorbance, or fluorescence of a cladding or coating material applied to a light-guiding core.

Unfortunately, such optical fibers are characterized by spatial transients for transmitted light which causes the sensitivity of chemically or physically sensitive fibers to vary from point to point along the fiber. This is particularly true of multi-mode fibers with lossy (e.g. absorber-doped) coatings where light does not reach equilibrium for a considerable distance. Such a varying response is due to a spatial transient, associated with the existence of radiation modes, and strong attenuation of higher order bound modes. Accordingly, sensor response over the length of the fiber is not constant.

BRIEF DESCRIPTION OF THE INVENTION

In accordance with the principles of the invention, the fraction of light lost per unit length may be controlled by controlling the physical design of the fiber. One use for this invention is to compensate for the spatial transient in distributed fiber optic sensors, wherein a constant sensitivity over the length of a distributed fiber sensor is achieved by introducing a change in the light-guiding characteristics of the fiber to compensate for the effects of spatial transients. Thus, for example, in one embodiment, a loss-compensated distributed optical fiber sensor comprises a core and a cladding where the core to cladding refractive index differential increases with length to compensate for the loss of higher order modes in the (multi-mode) fiber. As a result, a highly uniform, distributed sensor is realized.

DETAILED DESCRIPTION OF ILLUSTRATIVE EMBODIMNETS OF THE INVENTION

Multi-mode absorption based distributed sensors have an output response given by $$P \approx P_o \frac{V}{\alpha l} \qquad (1)$$

as is well known. In the equation, V is the fiber number given by $$V = ka\sqrt{n_{co}^2 - n_{cla}^2} \qquad (2)$$

where $P_o$ is the power at the input end of the fiber, P is the power at a distance 1 from the input end, a is the core radius, $\alpha$ is the absorption coefficient of the cladding, and $n_{co}$ and $n_{cla}$ are core and cladding refractive indices. Equation (1) is the generic response, which can be observed as a change in total transmitted light intensity using a simple detection scheme, observed as a plot of backscattered power versus length in an optical time domain reflectometer (OTDR), of a multi-mode optical fiber with an absorbing cladding. It is clear that the power lost per unit length at each position along a distributed optical fiber sensor is different from the power lost per unit length at any other position along the fiber.

Figure 1:
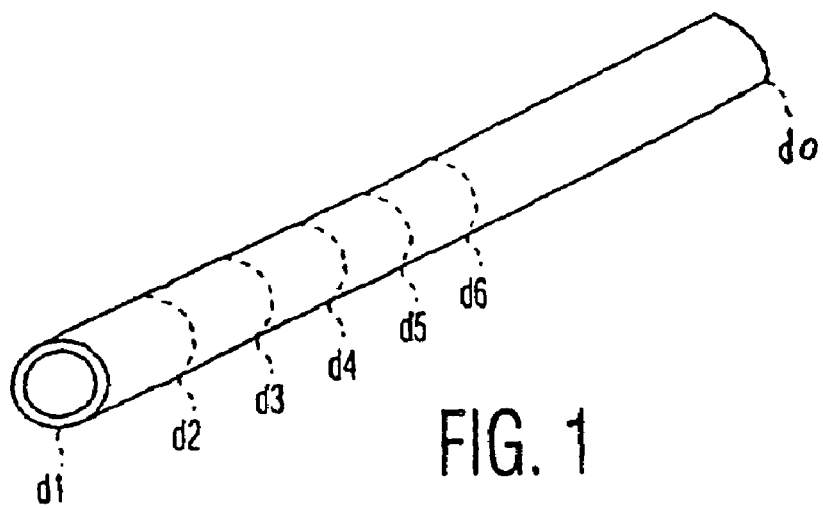
FIG. 1 is a schematic illustration of an optical fiber.

FIG. 1 shows a representative distributed optical fiber sensor. The power can be calculated for each of the positions from the input (di) to the output (do) and at any of the positions d2, d3, d4, d5, d6 ... in between. Accordingly, the power along the length of the fiber is given by:

$$P = P_o \exp\left(-\sum_{i=1}^{N} \int_0^l \alpha(z)\eta_i(z)\,dz\right) \quad (3)$$

where N is a common mathematical designation for the number of segments used for the calculation; it represents the number of positions to which the calculation is applied, and $n_i$ is the fraction of the power carried by core guided modes.

Figure 2:
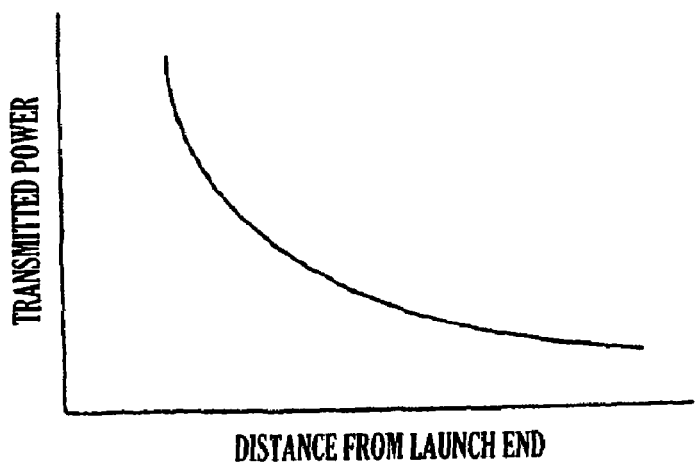
FIG. 2 is a graph of power transmitted vs. fiber position for prior art apparatus.
Figure 3:
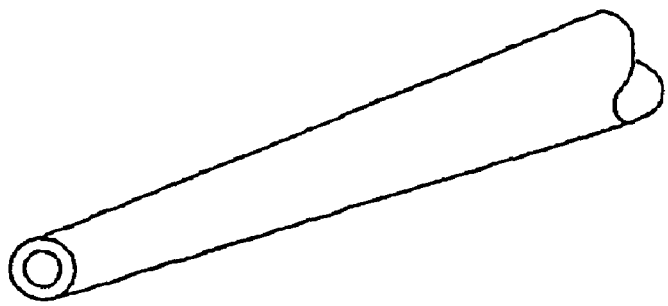
FIG. 3 is an illustrative embodiment in accordance with the principles of the invention.

In accordance with the present invention, a distributed, multi-mode optical fiber sensor can be made to exhibit a linear response in the dB scale. A linear response to changes in absorption may be achieved by compensating for the absorption fall off of FIG. 2 by:

a) Increasing the core/cladding refractive index ratio along the fiber length
b) Increasing the core diameter along the fiber length
c) Increasing the absorption coefficient of the sensor material in the cladding along the fiber length
d) Increasing the absorption coefficient of the cladding along the fiber length
e) Increasing the scattering coefficient of the core along the fiber length
f) Varying the parameters (a, b & c) together or in varying combinations FIG. 2 is a plot of power radiated per unit length versus fiber length l for a typical multimode fiber. The absorption clearly falls off. The absorption coefficient change is due to the fact that all modes in an optical fiber are attenuated differently. Modes closer to cut off (ie., modes that have an angle of incidence in the core/cladding boundary closer to 90 degrees) are attenuated quicker than modes far from cut off. In order to obtain an even attenuation as a function of length, coupling from lower order modes to higher order modes must occur. Even attenuation is achieved, for example, by increasing the core diameter as shown in FIG. 3 or by varying the core/cladding refractive index ratio or by increasing the absorption coefficient or scattering coefficient along the length of the fiber to compensate for the lower attenuation rate of modes that are increasingly far from cut off.

Figure 4:
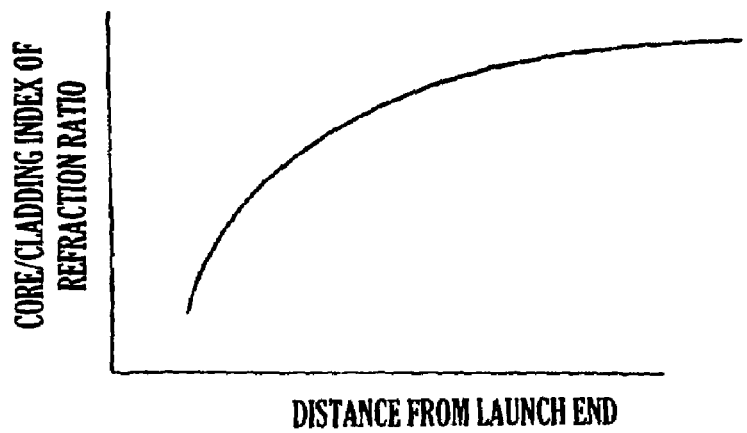
FIG. 4 is a graph of refractive index variation with distance from the launch end of a fiber in accordance with the principles of this invention.
Figure 5:
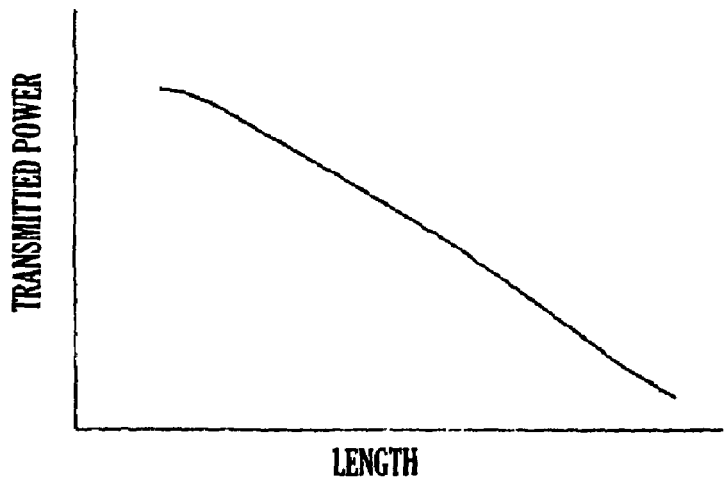
FIG. 5 is a plot of power transmitted vs. fiber position that results when light is launched into a fiber the refractive index of which varies as shown in FIG. 4.

FIG. 4 is a plot of $n_{co}/n_{cla}$ versus fiber length for a multi-mode, distributed sensor optical fiber in accordance with the principles of this invention. It is clear that an optical fiber so designed exhibits a power loss which is linear over the length of the fiber, for the combined effect of the spatial transient of FIG. 2 and the length-variation of fiber physical parameters (e.g., the refractive index, as shown in FIG. 4) is to linearize the power versus length curve (FIG. 5), thus creating a fiber sensor the sensitivity of which does not vary as a function of length.

Figure 6:
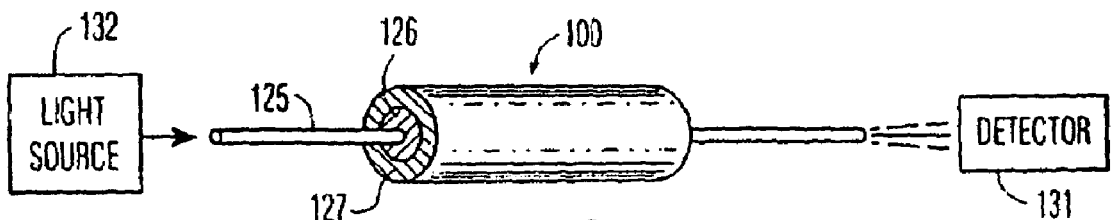
FIG. 6 is a block diagram of a system using the fiber of FIGS. 1 and 3.

FIG. 6 is a block diagram of sensor apparatus employing a fiber optic sensor of the type shown in FIG. 4. The fiber 100 includes a core 125 transmissive of electromagnetic radiation (e.g. light) and a cladding or sheath 126 of a permeable material. The index of refraction of sheath 126 is lower than that of core 125, and may vary with length. The fiber may include a coating 127 which also would be of a permeable material.

A reactant to be detected, causes a change of, for example, the intensity of light back scattered toward the end into which light is launched. The input light is launched, and the output light is detected by detector 131 as noted herein before.

Light energy is introduced at the input end of the fiber by, illustratively, a laser 132 and the properties of the light energy (e.g. intensity, wavelength—) are modified by interaction between material in the fiber sheath and the reactant to generate backscattered light characteristic of the reactant and the interaction with the sheath material.

Figure 7:
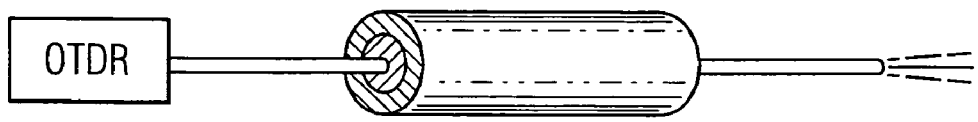
FIG. 7 is a block diagram of a further system using the fiber of FIGS. 1 and 3.
Figure 8:
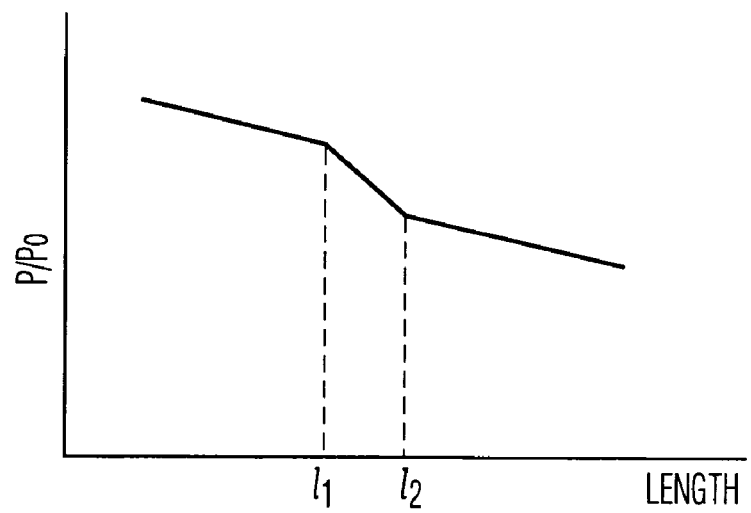
FIG. 8 is a plot of energy loss vs. fiber position that results when light is launched into the fiber of FIG. 5 when a section of the fiber is exposed to a target chemical substance.
Figure 9:
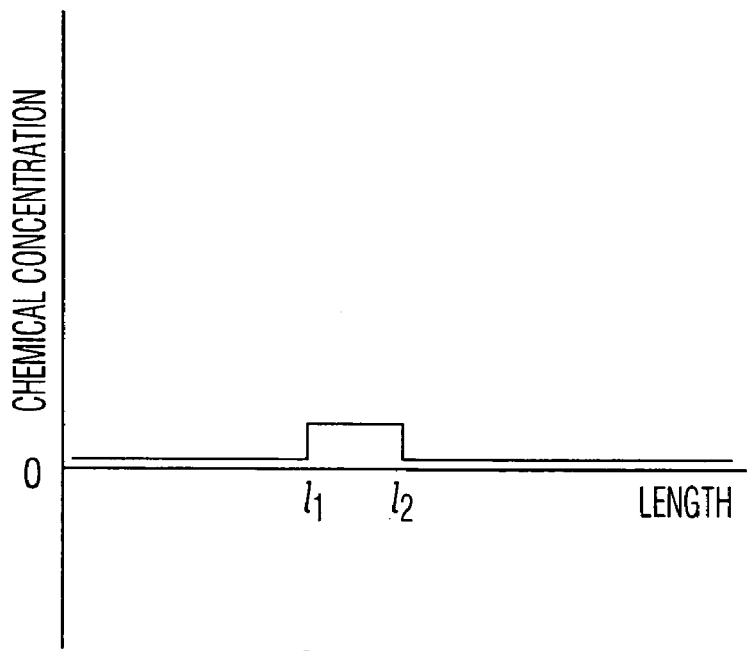
FIG. 9 is a plot of chemical concentration vs. fiber position that can be derived from FIG. 8.

The importance of structuring the fiber so that this interaction is constant over the length of the fiber is most clear in applications where the presence of a test chemical (reactant) may be at a point along the fiber and a cumulative effect over the length of the fiber is not an issue. The use of an ODTR, as shown in FIG. 7, permits the position of the reactant along the fiber to be determined as indicated in FIGS. 8 and 9. In addition, such a loss compensated sensor fiber can be used to accurately measure average chemical concentration over the entire fiber length by measuring the total light loss induced by the presence of the chemical using the system of FIG. 6. This is not possible for fibers the power versus length curve of which is nonlinear (e.g. FIG. 2). An optical fiber structured in accordance with this invention to exhibit a length-invariant response to such interactions is also advantageous for illumination applications and for applications in which an accumulated response is desired as in U.S. Pat. No. 4,321,057 issued Mar. 23, 1982 and in the above noted U.S. Pat. No. 4,834,496 where the portion of the length of fiber affected may be compared to some threshold for triggering an alarm.

An optical fiber having a core of F-2 Schott glass with a diameter of 100 micrometers and a cladding of polymer with a thickness of 20 micrometers was fabricated and a twenty meter length of the fiber was tested at 850 nm (active wavelength) as a moisture sensor. A reference wavelength of 1300 nm also was used. A dry reference measurement was made and then increasing lengths of 10 cm, 20 cm, and 50 cm were wetted. A final reading was taken after allowing the 50 cm wet length to air dry for one hour. At 1300 nm only a slight change (<1 dB) in output intensity occurs after an input signal propagates more than 10 meters along the fiber. A significant change of 2.4 dB is detected at 850 nm. The OTDR was able to determine the location of the moisture site to within 1 cm using 850 nm light and 1300 nm light was capable of being used to compensate for transmission changes due to effects other than moisture.

A PH-sensitive fiber was also tested, in a manner similar to that for the moisture-sensitive fiber, immersed in PH-7 and PH-10 buffer solutions. At 1300 NM there was virtually no change in output intensity. At 850 nm a substantial change of 1.2 dB occurred. The OTDR was able to locate the position of the buffer solution along the fiber to within 2 cms at 850 nm, and again the 1300 nm signal could be used as a "reference".

The ability to structure a fiber to control the fraction of light lost per unit length in accordance with the principles of this invention also permits a fiber to be constructed to provide an arbitrary power loss profile along the fiber. By so doing, a fiber sensor may be provided which is particularly sensitive at a predesignated position in the fiber.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations within the scope of the claims will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether or not the element, component, or step is explicitly recited in the Claims. No claim element herein is to be construed under the provisions of 35 U.S.C. Sec. 112, sixth paragraph, unless the element is expressly recited using the phrase "means for . . . " and in the absence of recitation of structure and no method or process step herein is to be construed under those provisions unless the step, or steps, are expressly recited using the phrase "step(s) for . . . "

What is claimed is:

1. An optical fiber, said fiber being a multi-mode single core fiber and having a core and sheath, said fiber having at least one parameter that varies from an input end of said fiber to an output end thereof in a manner to maintain a constant power loss per unit length over the length of said fiber.

2. An optical fiber as in claim 1 wherein said core is fabricated in a manner to be sensitive to a target chemical.

3. An optical fiber as in claim 1 wherein said sheath includes a cladding and said cladding is fabricated in a manner to be sensitive to a physical quantity.

4. An optical fiber as in claim 1 wherein said core is fabricated in a manner to be sensitive to a physical quantity.

5. An optical fiber as in claim 1 wherein said sheath includes a cladding and said cladding is fabricated in a manner to be sensitive to a target chemical.

6. An optical fiber as in claim 1 wherein said one parameter comprises an increase in the diameter of said core from said input end to said output end.

7. An optical fiber, said fiber being a multi-mode single core fiber and having a core and a cladding, said cladding being fabricated to be sensitive to a physical quantity, said fiber having at least one parameter that varies from an input end to an output end in a way calculated to make the power loss vary in a controlled way over the length of the fiber.

8. An optical fiber as in claim 7 wherein said one parameter comprises an increase in the diameter of said core from said input end to said output end.

* * * * *